(12) United States Patent
Joad et al.

(10) Patent No.: US 11,351,551 B2
(45) Date of Patent: Jun. 7, 2022

(54) MULTI-WELL PLATE ADAPTORS

(71) Applicants: ILLUMINA, INC., San Diego, CA (US); ILLUMINA CAMBRIDGE LIMITED, Cambridge (GB)

(72) Inventors: Andrew Joad, Huntingdon (GB); Daniel L. Fuller, Sudbury (GB); Paul Crivelli, San Diego, CA (US)

(73) Assignees: ILLUMINA, INC., San Diego, CA (US); ILLUMINA CAMBRIDGE LIMITED, Cambridge (GB)

( * ) Notice: Subject to any disclaimer, the term of this patent is extended or adjusted under 35 U.S.C. 154(b) by 237 days.

(21) Appl. No.: 16/626,138

(22) PCT Filed: Oct. 31, 2018

(86) PCT No.: PCT/US2018/058461
§ 371 (c)(1),
(2) Date: Dec. 23, 2019

(87) PCT Pub. No.: WO2019/089757
PCT Pub. Date: May 9, 2019

(65) Prior Publication Data
US 2020/0122147 A1    Apr. 23, 2020

Related U.S. Application Data

(60) Provisional application No. 62/581,066, filed on Nov. 3, 2017.

(51) Int. Cl.
*B01L 3/00* (2006.01)

(52) U.S. Cl.
CPC ............... *B01L 3/56* (2013.01); *B01L 3/5085* (2013.01); *B01L 2200/0631* (2013.01); *B01L 2300/0672* (2013.01); *B01L 2300/0829* (2013.01)

(58) Field of Classification Search
CPC ..... B01L 2200/0631; B01L 2300/0672; B01L 2300/0829; B01L 3/50255; B01L 3/5085;
(Continued)

(56) References Cited

U.S. PATENT DOCUMENTS 3,572,892 A * 3/1971 Metzgar ................. C12M 23/04
359/398
3,785,928 A     1/1974 Kessler
(Continued)

FOREIGN PATENT DOCUMENTS

WO    WO-98/55232 A1    12/1998
WO    WO-2011/127945 A1    10/2011

OTHER PUBLICATIONS

Axygen Product Selection Guide Issue 3, May 2017 (Year: 2017).*
(Continued)

*Primary Examiner* — Jennifer Wecker
*Assistant Examiner* — Jonathan Bortoli
(74) *Attorney, Agent, or Firm* — Marshall, Gerstein & Borun LLP

(57) ABSTRACT

Disclosed are multi-well plate inserts that can be used to separate solid debris, including paper punch containing a blood sample, from a liquid containing target biological molecules, such as nucleic acid molecules and proteins. Also provided are methods of using the insert, for example as part of a method that analyzes target biological molecules.

25 Claims, 10 Drawing Sheets

(58) Field of Classification Search
CPC ....... B01L 3/50853; B01L 3/56; C12M 23/12; C12M 23/38; C12M 25/04
See application file for complete search history.

(56) References Cited

U.S. PATENT DOCUMENTS

| | | | |
|---|---|---|---|
| 6,269,957 B1* | 8/2001 | Bowers | B01D 61/18 |
| | | | 210/321.6 |
| 6,528,302 B2* | 3/2003 | Turner | B01L 3/5085 |
| | | | 435/288.4 |
| 7,318,911 B2 | 1/2008 | Smith | |
| 8,501,462 B2 | 8/2013 | Eddington et al. | |
| 8,663,580 B2 | 3/2014 | Grenz et al. | |
| 2003/0129741 A1 | 7/2003 | Ramstad | |
| 2010/0233034 A1 | 9/2010 | Olivier et al. | |
| 2011/0136699 A1* | 6/2011 | Shirazi | B01L 3/50855 |
| | | | 506/39 |
| 2013/0323829 A1 | 12/2013 | Torterella | |
| 2016/0349244 A1 | 12/2016 | Zhang | |

OTHER PUBLICATIONS

Axygen™ 24- and 32-Well PCR Microplates Website Printout, 2021 (Year: 2021).*
Corning® FluoroBlok™ Cell Culture Inserts (2019). Retrieved from the Internet at: URL:https://www.corning.com/worldwide/en/products/life-sciences/products/permeable-supports/fluoro-blok.html.

* cited by examiner

- Test of Automated DBS Extraction protocol
- Few minor changes made to fix pipetting issue seen on first run
- Test to see if low yield before was solely sample or whether method was a factor
- 8 samples (1 donor – CS653)
- 4 samples were DBS and 4 were liquid blood
- Workflow:

MULTI-WELL PLATE ADAPTORS

CROSS-REFERENCE TO RELATED APPLICATION

This application is a 35 U.S.C. 371 National Stage of International Patent Application No. PCT/US2018/058461, filed Oct. 31, 2018, which itself claims the benefit of and priority to U.S. Provisional Patent Application No. 62/581,066, filed Nov. 3, 2017, the content of each of which is incorporated by reference herein in its entirety and for all purposes.

BACKGROUND

Blood samples are often collected on filter paper punches in dried blood spots (DBS). Formalin-fixed paraffin-embedded (FFPE) samples are often solubilized to extract target molecules, such as nucleic acid molecules. DBS and FFPE samples can be stored in well plates (e.g. 96-well plates) for bulk assays and patient arrays. In such assays, soluble material such as nucleic acid molecules can be extracted from the blood within the DBS or from the biological material (e.g., tissue) within the FFPE sample.

The problem of pipetting sample lysate a DBS- or FFPE sample-containing well is that the filter paper punch, tissue, paraffin particles, and/or other debris can get stuck on or in the pipet tip. Liquid handling robots, useful in well-plate assays with many multiple samples, do not have the finesse or visual or tactical feedback to avoid filter paper, paraffin, tissue, or other debris within a well plate. When pipetting small volumes using a liquid handling robot, the transfer of undesirable debris may interfere with aspiration, or the debris may stick to the outside of a pipette tip resulting in an accidental transfer of the material to an incorrect plate or well. Blockage of the tip with debris can also result in incomplete transfer of lysates into subsequent processing steps. Thus, ideally, aspirating solution from a DBS- or FFPE sample-containing well may avoid the filter paper punch, tissue, paraffin particles, and/or other debris to prevent blockage of the pipette tip and maintain accurate pipetting volumes.

SUMMARY

Provided in some examples herein are multi-well plate adaptors or inserts, and methods of their use, for example in separation of solid debris from liquid aspirate in well plate assays.

Provided herein are multi-well plate adaptors or inserts that can be used with multi-well plate, which can be used when a lysate or aspirate is to be removed from the multi-well plate containing solid debris. In some examples, the multi-well plate adaptors or inserts are designed for use with a 96-well plate (such as three adaptors per 96-well plate), a 12-well plate, a 24-well plate, a 48-well plate, or a 384-well plate (such as one adaptor per 12- or 24-well plate; one, two or three adaptors per 48-well plate; or 12 adaptors per 384-well plate). For example, the well plate adaptor or insert can be configured such that it can nest on top of a multi-well plate (e.g., 96-well plate) such that each of the plurality of hollow extensions of the adaptor/insert protrudes into a separate individual well of the multi-well plate (in some cases without touching the bottom of the multi-well plate).

In one example, the multi-well plate adaptor includes two or more component parts, such as at least three, at least four, at least five, or at least ten component parts, such as 2, 3, 4, 5, 6, 7, 8, 9, 10, 11, 12, 13, 14, 15, 16, 17, 18, 19 or 20 component parts. Each component part can include a top surface with hollow conical protrusions extending therefrom, the axis of the conical protrusions being perpendicular to the top surface. Each conical protrusion of the component part can include an angled tip at the end distal from the top surface, the angled tip comprising one or more holes, and one or more ridges on an outer surface of the angled tip.

In some examples, the top surface of each component part has a length of about 75 mm-95 mm, a width of about 30 mm-40 mm, and a height of about 30 mm-40 mm. In some examples, the distance that the protrusions (e.g., conical) extend from the top surface is shorter than the depth of the wells of the multi-well plate to which it is configured for. In some examples, the distance the protrusions (e.g., conical) extend from the top surface is about 15 mm-35 mm. In some examples, the inner diameter of the hollow protrusions (e.g., conical) is such that it can accommodate a pipette tip or other aspiration device. In some examples, the one or more holes of the angled tip has an open dimension of about 0.6 mm to 0.8 mm. In some examples, the angled tip includes a central hole at the distal end and multiple longitudinal holes radiating symmetrically therefrom, each hole separated by a portion of the angled tip, and wherein the portion of the angled tip separating each of the longitudinal holes further comprises the ridges on an outer surface of the angled tip. In some examples, the central hole has a diameter of about 0.6 mm-1 mm and the longitudinal holes comprise a minimal open dimension of about 0.6 mm-1 mm.

In one example, the multi-well plate insert for aspiration of lysate includes two or more insert components, such as at least three, at least four, at least five, or at least ten insert components, such as 2, 3, 4, 5, 6, 7, 8, 9, 10, 11, 12, 13, 14, 15, 16, 17, 18, 19 or 20 insert components. Each insert component can include a rectangular top surface with hollow extensions protruding therefrom, wherein the main axis of the hollow extensions is at least substantially perpendicular (including perfectly perpendicular) to a plane of the rectangular top surface. In one configuration, each insert component comprises 32 hollow extensions arranged in a grid with four hollow extensions along a short edge of the rectangular top surface and eight hollow extensions along the long edge of the rectangular top surface. The long edge of the rectangular top surface can be adapted to fit with the long edge of the rectangular top surface of another insert component. The hollow extensions can include at their terminus a distal tip with one or more perforations, and the distal tip can further include, on its outer surface, one or more ridges extending away from the main body of the distal tip. The one or more perforations can include a central hole at the distal tip, multiple longitudinal holes radiating symmetrically therefrom, or both, wherein each perforation is separated by a portion of the distal tip.

A main body, which can be a solid surface, of the hollow extensions can be an elongate frusto-conical extension, wherein the distal tip extends at least substantially conically from the smaller diameter end of the hollow extension. In some examples, the one or more ridges do not extend beyond the distal tip onto the main body of the hollow extensions. In some examples, the hollow extensions do not include or are not made of a mesh or fiber insert (e.g., screen). In some examples, the one or more perforations on the hollow extensions are sized to allow a lysate to flow through and to prevent passage of a particulate in a well of the well plate (such as a reducing pass of particulate by at least 50%, at least 60%, at least 70%, at least 80%, at least 90%, at least 95%, at least 98%, at least 99%, or even 100%), and in some examples have a minimal open dimension of about 0.6 mm-0.8 mm. In some examples, the one or more ridges of the distal tip are capable of piercing a sterile seal of the well plate or propagating a hole or perforation formed by a pipette tip.

In one example, the multi-well plate insert (e.g., lysate isolation plate adaptor) includes three identical components parts, wherein each components part includes a planar rectangular main body with 32 elongate extensions protruding in a grid pattern therefrom, wherein a main axis of each elongate extension is perpendicular to the planar rectangular main body. Each elongate extension has a rounded tip with a plurality of holes therein, each hole in some examples having a minimal open dimension of about 0.6 mm-0.8 mm and one or more angled spines on an exterior surface of the rounded tip.

Provided herein is a multi-well plate adaptor, comprising two or more component parts, each component part comprising a top surface with hollow conical protrusions extending therefrom, the axis of the conical protrusions being perpendicular to the top surface; and each hollow conical protrusion comprising an angled tip at the end distal from the top surface, the angled tip comprising one or more holes, and one or more ridges on an outer surface of the angled tip.

Provided herein is a well plate insert, comprising, two or more insert components, each insert component comprising a rectangular top surface with hollow extensions protruding therefrom, wherein a main axis of the hollow extensions is at least substantially perpendicular to a plane of the rectangular top surface; the hollow extensions having at their terminus a distal tip with one or more perforations; the distal tip further comprising, on its outer surface, one or more ridges extending away from the main body of the distal tip; and a long edge of the rectangular top surface adapted to fit with the long edge of the rectangular top surface of another insert component.

A lysate isolation plate adaptor, comprising three identical components parts, each comprising a planar rectangular main body with 32 elongate extensions protruding in a grid pattern therefrom, wherein a main axis of each elongate extension is at least substantially perpendicular to the planar rectangular main body; each elongate extension having a rounded tip with a plurality of holes therein, each hole having a minimal open dimension of 0.6 mm-0.8 mm; and one or more angled spines on an exterior surface of the rounded tip.

Also provided are methods of using the disclosed multi-well plate inserts, for example in methods that include obtaining or collecting a lysate containing one or more target biological molecules (such as a nucleic acid molecule or protein, such as DNA, RNA, or antibody). For example, the method can include adding or placing one or more of the disclosed multi-well plate inserts on top of a multi-well plate containing a lysate (such as from a DBS or FFPE sample), such that each extension or protrusion of the multi-well plate inserts protrude into a single well of the multi-well plate (e.g., one extension per well). In some examples, the one or more disclosed multi-well plate inserts lock onto the multi-well plate. However, in some examples the one or more disclosed multi-well plate inserts simply sit on top of the multi-well plate. This allows the lysate, but not debris, in the well of the multi-well plate to flow into the extensions/protrusions via the holes in the extensions/protrusions. The method can then include introducing a pipette tip (or other aspiration device) into each extension/protrusion, to allow for collection of the lysate, without the debris.

DETAILED DESCRIPTION

Figure 1:
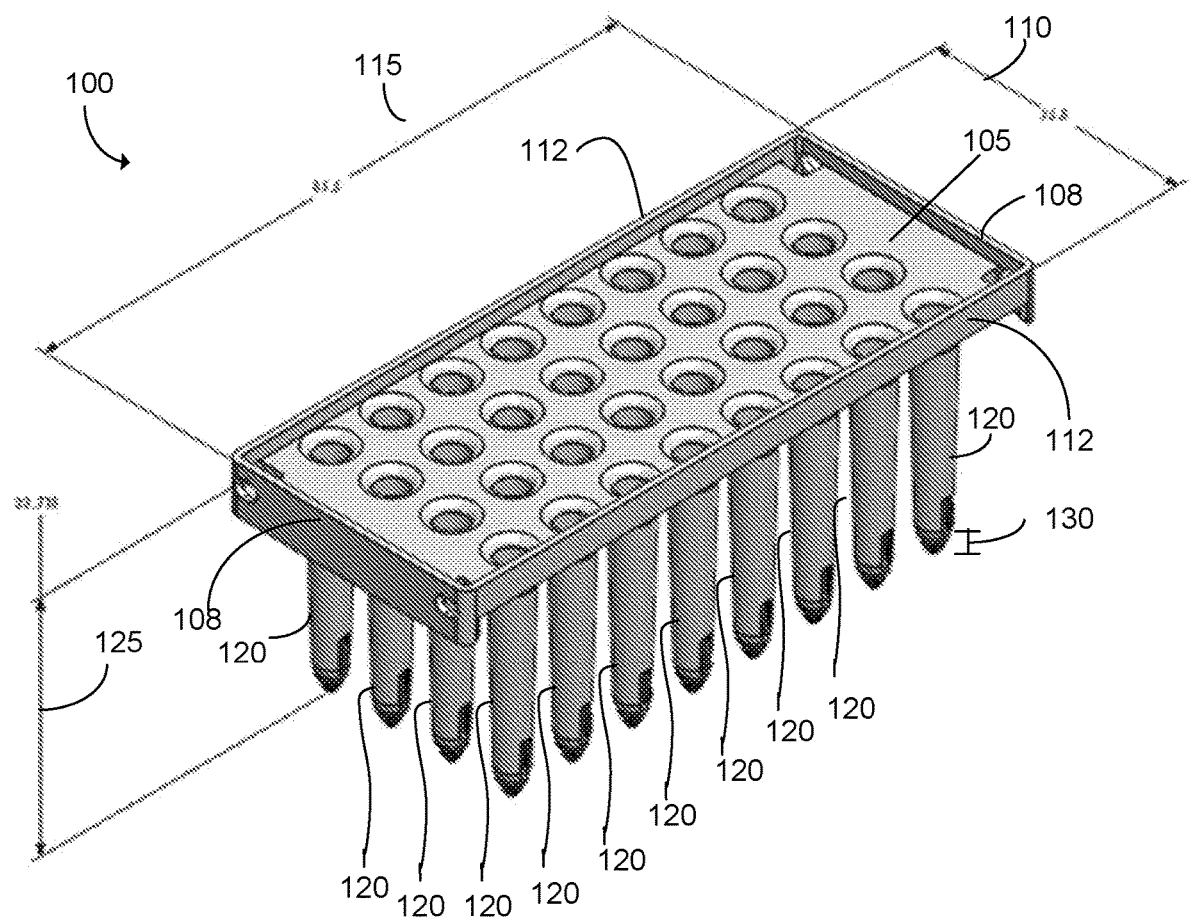
FIG. 1 is a schematic drawing showing an example single component part 100 of a multi-well plate insert.

Unless otherwise noted, technical terms are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a multi-well insert" means "including a multi-well insert" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, are herein incorporated by reference.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

In order to facilitate review of the various examples of the disclosure, the following explanations of specific terms are provided:

Dried Blood Spot:

A blood sample that is dried and present on a solid support, such as a filter paper card or disk. In some examples, the blood can be obtained from a prick of the heel, toe, or finger, or from a vein or artery, applied to the solid support (e.g., filter paper), and allowed to dry (for example for several hours). In some examples, the blood is from a mammalian subject.

Isolated:

An "isolated" biological component (such as a protein, nucleic acid molecule, or cell) has been substantially separated, produced apart from, or purified away from other biological components in the cell or tissue of an organism in which the component occurs, such as other cells, chromosomal and extrachromosomal DNA and RNA, and proteins. Isolated proteins, nucleic acids, or cells in some examples are at least 50% pure, such as at least 75%, at least 80%, at least 90%, at least 95%, at least 98%, or at least 100% pure. In some examples, an isolated biological component is present in a liquid lysate.

Nucleic Acid (Molecule or Sequence):

A deoxyribonucleotide or ribonucleotide polymer or combination thereof including without limitation, cDNA, mRNA, miRNA, rRNA, tRNA, genomic DNA, and synthetic (such as chemically synthesized) DNA or RNA. A nucleic acid molecule can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides.

Polypeptide, Peptide and Protein:

Refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

Purified:

The term purified does not require absolute purity; rather, it is intended as a relative term. Thus, for example, a purified protein preparation is one in which the protein (is more enriched than the protein is in its natural environment within a cell. In one example, a preparation is purified such that the protein represents at least 50% of the total protein content of the preparation. In some examples, a purified protein is present in a liquid lysate.

Sample:

Refers to any biological sample (taken from a biological organism) or environmental sample (taken from an environment, such as a water, soil, or air sample). A biological sample is a sample obtained from a subject (such as a human or veterinary subject) that is a biological organism. In some examples, the sample is fixed, such as an FFPE sample. In particular examples, the biological sample is a biological fluid sample from any bodily fluid, such as peripheral blood, sera, plasma, ascites, urine, cerebrospinal fluid (CSF), sputum, saliva, bone marrow, synovial fluid, aqueous humor, amniotic fluid, cerumen, breast milk, bronchioalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. A biological sample may also include the blastocyl cavity, umbilical cord blood, or maternal circulation which may be of fetal or maternal origin. The biological sample may also be a tissue sample or biopsy (including a fine needle aspirate). In some examples, the biological sample is an FFPE tumor sample. In some examples, the biological sample is a DBS. Such samples can be used to detect a target molecule, such as a target nucleic acid molecule or target protein. In some examples, such samples are used as a source of nucleic acid molecules from which a target nucleic acid molecule can be sequenced.

Sample:

Biological specimens such as samples containing biomolecules, for example nucleic acid molecules (e.g., genomic DNA, cDNA, RNA, and/or mRNA). Example samples are those containing cells or cell lysates from a subject (and which may contain one or more pathogens), such as peripheral blood (or a fraction thereof such as plasma or serum), urine, saliva, sputum, tissue biopsy, cheek swabs, fecal specimen (e.g., stool sample), respiratory specimen, surgical specimen, fine needle aspirates, amniocentesis samples and autopsy material. Also includes other types of samples, such as environmental samples (e.g., soil, air, water), and food samples. Samples can be applied to a solid support, for example to store nucleic acid molecules present in the sample.

Subject:

A vertebrate, such as a mammal, for example a human. Mammals include, but are not limited to, murines, simians, humans, farm animals, sport animals, and pets. In one example, the subject is a non-human mammalian subject, such as a monkey or other non-human primate, mouse, rat, rabbit, pig, goat, sheep, dog, cat, horse, or cow. In some examples, the subject has or is suspected of being infected with a pathogen (such as having a viral, bacterial, fungal, or parasitic infection). In some examples, the subject has or is suspected of having cancer. Thus, subjects can serve as a source of samples analyzed using the disclosed methods and devices.

Overview

Pipetting a liquid material (e.g., cell or tissue lysate) from a well containing a dried blood spot or tissue biopsy (e.g.

FFPE tissue) can result in debris (e.g., the spot or parts of the spot (e.g. filter paper), tissue, or paraffin particles) being stuck on or in the pipetting tip. The multi-well plate inserts of the present disclosure reduce this problem. The multi-well plate inserts described herein rests on top of a multi-well plate containing a liquid material (e.g., cell or tissue lysate) in the wells, and allows pipetting of a liquid material (e.g., cell or tissue lysate) without pipetting debris present in the well. The multi-well plate inserts disclosed herein can be used with robotic sample handing.

The multi-well plate inserts provided herein are adapted to fit on top of a multi-well plate. The inserts include projections that insert into the wells of the plate. Holes or openings in the projections are small enough to allow liquid in well, but not debris, to enter the projections. The resulting liquid can then be removed, for example by pipetting. Thus, if the well contains a dried blood spot, tissue debris, filter paper, nitrocellulose paper, or paraffin particles, these do not enter the projections of the insert, and are not removed during sample handling.

Multi-Well Plate Adaptors

Provided herein are multi-well plate adaptors (also referred to herein as inserts, as they are introduced or inserted into a multi-well plate when in use) that can be used with a multi-well plate, for example when a liquid material (such as lysate or aspirate) that may contain undesirable debris is to be removed from the multi-well plate. In some examples, the multi-well plate adaptors or inserts are designed for use with a 96-well plate (such as three adaptors per 96-well plate), a 6-well plate (such as one adaptor per 6-well plate), a 12-well plate (such as one adaptor per 12-well plate), a 24-well plate (such as one adaptor per 24-well plate), a 48-well plate (such as one, two or three adaptors per 48-well plate), or a 384-well plate (such as 12 adaptors per 384-well plate). For example, the multi-well plate adaptor or insert can be configured such that it can nest on top of a multi-well plate (e.g., 96-well plate), such that each hollow extension of the adaptor protrudes into an individual well of the multi-well plate (e.g., one extension per well).

In one example, the multi-well plate adaptor or insert includes two or more component parts or insert components, such as at least three, at least four, at least five, or at least ten component parts or insert components, such as 2, 3, 4, 5, 6, 7, 8, 9, 10, 11, 12, 13, 14, 15, 16, 17, 18, 19 or 20 component parts or insert components. Each component part or insert component can include a top surface (such as a rectangular top surface) having hollow protrusions (such as conical, round, square, or rectangular shaped hollow protrusions) extending (or hollow extensions protruding) therefrom. The top surface can include four sides or edges, such as two long and two short sides or edges (e.g., thereby forming a rectangle). The first long edge of the top surface (such as the long edge of a rectangular top surface) of a first insert component can be adapted to fit with a first long edge of the top surface (such as the long edge of a rectangular top surface) of a second insert component. In addition, a second long edge of the top surface (such as the long edge of a rectangular top surface) of a first insert component can be adapted to fit with a long edge of the top surface (such as the long edge of a rectangular top surface) of a third insert component.

In some examples, the top surface (such as a rectangular top surface) of each component part or insert component has a length of at least about 75 mm, at least about 80 mm, at least about 90 mm, or at least about 95 mm, such as about 75 mm to about 95 mm, about 80 mm to about 95 mm, about 85 mm to about 95 mm, about 85 mm to about 90 mm, such as 75±0.5 mm, 76±0.5, mm, 77±0.5 mm, 78±0.5 mm, 79±0.5 mm, 80±0.5 mm, 81±0.5 mm, 82±0.5 mm, 83±0.5 mm, 84±0.5 mm, 85±0.5 mm, 86±0.5 mm, 87±0.5, mm 88±0.5 mm, 89±0.5 mm, 90±0.5 mm, 91±0.5 mm, 92±0.5 mm, 93±0.5 mm, 94±0.5 mm, or 95±0.5 mm, or about 75±0.1 mm, 76±0.1, mm, 77±0.1 mm, 78±0.1 mm, 79±0.1 mm, 80±0.1 mm, 81±0.1 mm, 82±0.1 mm, 83±0.1 mm, 84±0.1 mm, 85±0.1 mm, 86±0.1 mm, 87±0.1, mm 88±0.1 mm, 89±0.1 mm, 90±0.1 mm, 91±0.1 mm, 92±0.1 mm, 93±0.1 mm, 94±0.1 mm, or 95±0.1 mm, in some examples 80±1 mm, 81±1 mm, 82±1 mm, 83±1 mm, 84±1 mm, 85±1 mm, 85.5±1 mm, 86±1 mm, 87±1, mm 88±1 mm, 89±1 mm, or 90±1 mm. Other values are also possible. In some examples, the top surface (such as a rectangular top surface) of each component part or insert component has a length of 85.5±1 mm, 85.5±0.5 mm 85.5±0.3 mm, 85.5±0.2 mm or 85.5±0.1 mm. In some examples, the top surface (such as a rectangular top surface) of each component part or insert component has a width of about at least about 25 mm, at least about 30 mm, at least 33 mm, at least about 35 mm, at least about 36 mm, or at least about 37 mm, such as about 25 mm to about 40 mm, about 25 mm to about 36 mm, about 28 mm to about 36 mm, about 34 mm to about 36 mm, such as 25±0.5 mm, 26±0.5, mm, 27±0.5 mm, 28±0.5 mm, 29±0.5 mm, 30±0.5 mm, 31±0.5 mm, 32±0.5 mm, 33±0.5 mm, 34±0.5 mm, 35±0.5 mm, 36±0.5 mm, 37±0.5 mm, or 38±0.5 mm, or 25±0.1 mm, 26±0.1, mm, 27±0.1 mm, 28±0.1 mm, 29±0.1 mm, 30±0.1 mm, 31±0.1 mm, 32±0.1 mm, 33±0.1 mm, 34±0.1 mm, 35±0.1 mm, 36±0.1 mm, 37±0.1 mm, or 38±0.1 mm. In some examples, the top surface (such as a rectangular top surface) of each component part or insert component has a width of 35.8±0.5 mm, 35.8±0.3 mm, 35.8±0.2 mm or 35.8±0.1 mm, such as 35.8 mm+0.2 mm or −0.5 mm. Other values are also possible. In some examples, the top surface (such as a rectangular top surface) of each component part or insert component has a height of at least about 25 mm, at least about 30 mm, at least 33 mm, at least about 35 mm, or at least about 40 mm, such as about 25 mm to about 40 mm, about 25 mm to about 35 mm, about 28 mm to about 35 mm, about 32 mm to about 34 mm, such as 25±0.5 mm, 26±0.5, mm, 27±0.5 mm, 28±0.5 mm, 29±0.5 mm, 30±0.5 mm, 31±0.5 mm, 32±0.5 mm, 33±0.5 mm, 34±0.5 mm, 35±0.5 mm, 36±0.5 mm, 37±0.5, mm 38±0.5 mm, 39±0.5 mm, 40±0.5 mm, or 25±0.1 mm, 26±0.1, mm, 27±0.1 mm, 28±0.1 mm, 29±0.1 mm, 30±0.1 mm, 31±0.1 mm, 32±0.1 mm, 33±0.1 mm, 34±0.1 mm, 35±0.1 mm, 36±0.1 mm, 37±0.1, mm 38±0.1 mm, 39±0.1 mm, 40±0.1 mm, 41±0.1 mm, 42±0.1 mm, 43±0.1 mm, 44±0.1 mm, or 45±0.1 mm. In some examples, the top surface (such as a rectangular top surface) of each component part or insert component has a height of 33.7±0.3 mm, 33.7±0.2 mm, 33.7±0.1 mm, 33.718±0.3 mm, 33.718±0.2 mm or 33.718±0.1 mm. Other values are also possible.

The top surface includes a plurality of hollow protrusions/extensions having a distal tip, wherein the axis of the protrusions/extensions is at least substantially perpendicular to the top surface. In some examples, the protrusions/extensions are conical, rectangular, circular, or square. For example, the main body, which can be a solid surface, of the hollow extensions can be an elongate frusto-conical extension, wherein the distal tip extends substantially conically from the smaller diameter end of the hollow extension. In some examples, the distance that the protrusions/extensions (e.g., conical, rectangular, circular, or square) extend from the top surface is shorter than the depth of the wells of the multi-well plate. In some examples, the distance the protrusions (e.g., conical, rectangular, circular, or square) extend from the top surface of each component is at least about 10 mm, at least about 12 mm, at least 15 mm, at least about 20 mm, at least about 25 mm, at least about 30 mm, at least about 35 mm, or at least about 40 mm, such as about 10 mm to about 30 mm, about 12 mm to about 30 mm, about 15 mm to about 30 mm, about 25 mm to about 35 mm, about 29 mm to about 30 mm, such as 10±0.5 mm, 11±0.5, mm, 12±0.5 mm, 13±0.5 mm, 14±0.5 mm, 15±0.5 mm, 16±0.5 mm, 17±0.5 mm, 18±0.5 mm, 19±0.5 mm, 20±0.5 mm, 21±0.5 mm, 22±0.5, mm 23±0.5 mm, 24±0.5 mm, 25±0.5 mm, 26±0.5 mm, 27±0.5 mm, 28±0.5 mm, 29±0.5 mm, 30±0.5 mm, 31±0.5 mm, 32±0.5 mm, 33±0.5 mm, 34±0.5 mm, 35±0.5 mm, or 10±0.1 mm, 11±0.1, mm, 12±0.1 mm, 13±0.1 mm, 14±0.1 mm, 15±0.1 mm, 16±0.1 mm, 17±0.1 mm, 18±0.1 mm, 19±0.1 mm, 20±0.1 mm, 21±0.1 mm, 22±0.1, mm 23±0.1 mm, 24±0.1 mm, 25±0.1 mm, 26±0.1 mm, 27±0.1 mm, 28±0.1 mm, 29±0.1 mm, 30±0.1 mm 31±0.1 mm, 31±0.5 mm, 33±0.1 mm, 34±0.1 mm, or 35±0.1 mm. In some examples, the distance the conical protrusions extend from the top surface of each component is 29.715±0.5 mm 29.715±0.3 mm, 29.715±0.2 mm or 29.715±0.1 mm. Other values are also possible.

The axis of the conical protrusions is at least substantially perpendicular to the top surface. For example, the main axis of the hollow extensions/protrusions is at least substantially perpendicular to a plane of a rectangular top surface. In one example, each insert component or part has 32 hollow extensions/protrusions arranged in a grid with four hollow extensions/protrusions along a short edge of the rectangular top surface and eight hollow extensions/protrusions along the long edge of the rectangular top surface. In one example, each insert component or part has 6 hollow extensions/protrusions arranged in a grid with two hollow extensions/protrusions along a short edge of the rectangular top surface and three hollow extensions/protrusions along the long edge of the rectangular top surface. In one example, each insert component or part has 12 hollow extensions/protrusions arranged in a grid with two hollow extensions/protrusions along a short edge of the rectangular top surface and six hollow extensions/protrusions along the long edge of the rectangular top surface. In one example, each insert component or part has 24 hollow extensions/protrusions arranged in a grid with four hollow extensions/protrusions along a short edge of the rectangular top surface and six hollow extensions/protrusions along the long edge of the rectangular top surface. In one example, each insert component or part has 48 hollow extensions/protrusions arranged in a grid with six hollow extensions/protrusions along a short edge of the rectangular top surface and eight hollow extensions/protrusions along the long edge of the rectangular top surface. In one example, each insert component or part has 96 hollow extensions/protrusions arranged in a grid with eight hollow extensions/protrusions along a short edge of the rectangular top surface and 12 hollow extensions/protrusions along the long edge of the rectangular top surface.

Each conical protrusion/extension of the component part/insert can include an angled tip at the end distal from the top surface. The angled tip of each conical protrusion/extension can include one or more holes or perforations, and one or more ridges on an outer surface of the angled tip. For example, the hollow extensions/protrusions can include at their terminus a distal tip with one or more perforations or holes, and the distal tip can further include, on its outer surface, one or more ridges extending away from the main body of the distal tip. In some examples, the hollow extensions do not include or are not made of a mesh or fiber insert (such as a screen). Thus, for example, the holes/perforations are in some examples are not formed by (or do not include) a mesh or fiber insert (such as a screen).

The opening afforded by the holes/perforations can be sized to allow a lysate (or other liquid) to flow through (e.g., enter) into the interior of the hollow extensions/protrusions, while preventing passage of particulate into the interior of the hollow extensions/protrusions. Instead, particulate or debris (such as filter paper or paraffin) present in the lysate (or other liquid) in the well of a multi-well plate remains on the exterior of the hollow extensions/protrusions. In some examples the holes or perforations are substantially circular, oval, triangular, square, or rectangular. In some examples the holes/perforations are substantially rectangular or longitudinal, with the end furthest from the top surface pointed, for example the holes/perforations can include two parallel sides longer than a short end nearer to the top surface, and a pointed end further from the top surface. In some examples, each hole/perforation has a minimal open dimension of about 0.6 mm to 1 mm, such as 0.6 mm to 0.8 mm, 0.7 mm to 0.75 mm, such as 0.6 mm, 0.65 mm, 0.7 mm, 0.75 mm or 0.8 mm. In one example, each hollow extension/protrusion includes at its terminus a distal tip at least two holes/perforations, at least three holes/perforations, at least four holes/perforations, at least five holes/perforations, at least 10 holes/perforations, or at least 20 holes/perforations, such as 2, 3, 4, 5, 6, 7, 8, 9, 10, 11, 12, 13, 14, 15, 16, 17, 18, 19 or 20 holes/perforations. In one example, the distal tip of each hollow extension/protrusion includes at its terminus hole/perforation, and can include two or more additional holes/perforations above the terminal hole/perforation (for example in an alternating arrangement with the one or more ridges). In some examples, the inner diameter of the hollow conical protrusions is such that it can accommodate a pipette tip (or other aspiration device). In some examples, the one or more holes/perforations of the angled tip has an open dimension of about 0.6 mm to 0.8 mm. In some examples, the angled tip includes a central hole at the distal end and multiple longitudinal holes radiating symmetrically therefrom, each hole separated by a portion of the angled tip, and wherein the portion of the angled tip separating each of the longitudinal holes further comprises the ridges on an outer surface of the angled tip. In some examples, the central hole has a diameter of about 0.6 mm-1 mm and the longitudinal holes comprise a minimal open dimension of about 0.6 mm-1 mm.

Each conical protrusion/extension of the component part/insert can include on its outer surface one or more ridges, such as on the outer surface of the angled tip. In some examples, the one or more ridges do not extend beyond the distal tip onto the main body of the hollow extensions. In some examples, each protrusion/extension includes at least two ridges, such as at least three, at least four, or at least five ridges, such as 2, 3, 4, 5, 6, 7, 8, 9 or 10 ridges. The one or more ridges of the distal tip can be capable of piercing a sterile seal of the well plate or propagating a hole or perforation formed by a pipette tip. In some examples, the angled tip includes alternating ridges and holes/perforations.

In one example, the multi-well plate insert (or lysate isolation plate adaptor) includes three identical components parts, wherein each components part includes a planar rectangular main body with 32 elongate extensions protruding in a grid pattern therefrom, wherein a main axis of each elongate extension is perpendicular to the planar rectangular main body. Each elongate extension has a rounded tip with a plurality of holes therein, each hole having a minimal open dimension of about 0.6 mm to 0.8 mm and one or more angled spines on an exterior surface of the rounded tip.

FIGS. 1 to 7 show an example single component part of a multi-well plate adaptor or insert and parts thereof. Each of FIGS. 1 to 7 are to scale. FIG. 1 shows an example single component 100 of a multi-well plate insert. In this illustrated example, component 100 could be one of three identical components used with a 96-well plate, each individual component 100 containing 32 protrusions and covering a third of the 96-well plate. However, one skilled in the art will recognize that the features provided herein can be adapted for other multi-well plates (such as a 12-well plate, a 24-well plate, a 48-well plate, or a 384-well plate), and that other numbers of component parts can be fashioned per multi-well plate. For example, the multi-well plate adaptors or inserts designed for use with a 96-well plate could include three adaptors per 96-well plate, the multi-well plate adaptors or inserts designed for use with a 6-well plate could include one adaptors per 6-well plate, the multi-well plate adaptors or inserts designed for use with a 12-well plate could include one adaptor per 12-well plate, the multi-well plate adaptors or inserts designed for use with a 24-well plate could include one adaptor per 24-well plate, the multi-well plate adaptors or inserts designed for use with a 48-well plate could include two or three or four adaptors per 48-well plate, and the multi-well plate adaptors or inserts designed for use with a 384-well plate could include 12 adaptors per 96-well plate.

As shown in FIG. 1, the component 100 contains a top surface 105. The top surface 105 can be substantially planar and largely rectangular. In some examples, the top surface 105 is flat. In one example, component 100 has two short sides 108 with width 110, such as a width of about at least about 25 mm, such as about 35.8 mm as shown in FIG. 1. In one example, component 100 has two long sides 112 with a length 115, such as length 115 of at least about 75 mm, such about 85.5 mm as shown in FIG. 1. The component 100 has a height 125, such as a height 125 of at least about 30 mm, such about 33.718 mm as shown in FIG. 1.

As shown in FIG. 1, extending from the at least substantially planar top surface 105 are a number of elongate extensions or protrusions 120. Each protrusion/extension 120 is hollow and includes an inner and outer surface (see FIG. 4) and terminates in an angled or tapered tip 130. The protrusions/extensions 120 can extend away from the at least substantially planar top surface 105 in a direction such that their main axis is perpendicular to the plane of the top surface 105. The protrusions/extensions 120 can be of a shape that matches the well into which the adaptor inserts (e.g., can be conical, circular, rectangular, or square) in shape, and can for example accommodate at least a portion of a pipette tip or other aspiration device (such as a 150 µl pipette tip, such as with a length of about 65 mm, and an inner tip orifice of about 0.4 mm). The number of protrusions/extensions 120 per single component 100 can vary, but the total number of protrusions/extensions 120 in all of the single components 100 used per multi-well plate is the same as the number of wells in the multi-well plate. Thus, for example, if three single components 100 are used for a single a 96-well plate, each single component 100 has 32 protrusions/extensions 120. In addition, the protrusions/extensions 120 are arranged in rows and columns in the same format as the target multi-well plate. For example, a 96-well plate has 8 rows and 12 columns, and thus the individual components 100 are designed such that when used together (e.g., 3 components 100 per 96-well plate) result in an arrangement of 8 rows and 12 columns of individual protrusions/extensions 120.

Figure 2A:
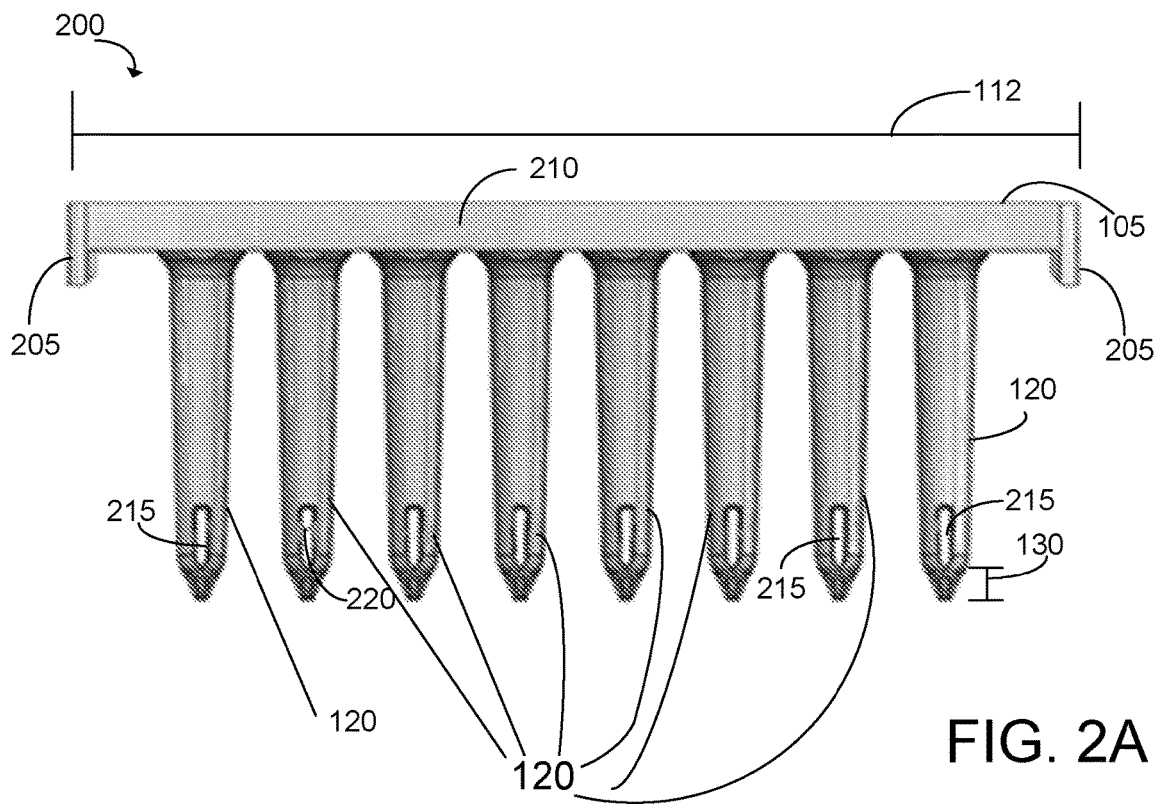
FIG. 2A is a schematic drawing showing a side view 200 of the long side 112 of an example single component 100 of multi-well plate insert.
Figure 2B:
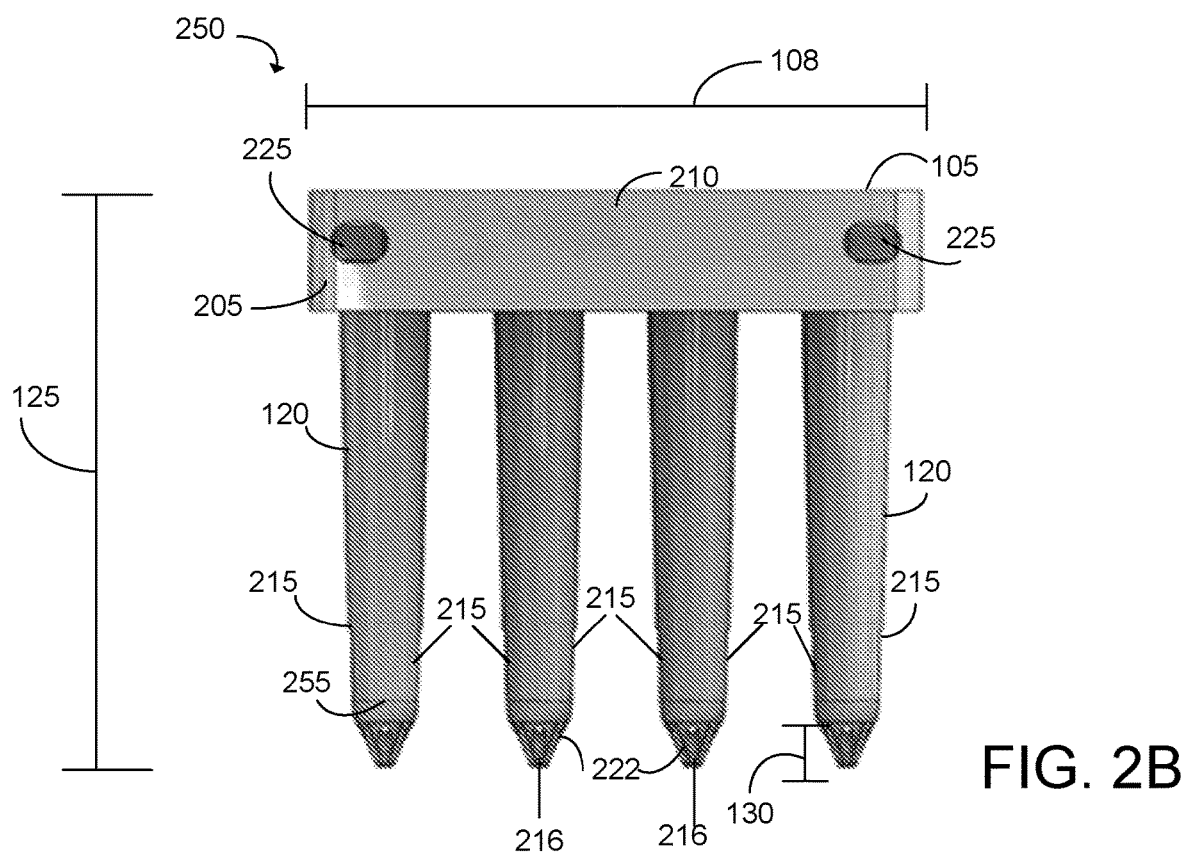
FIG. 2B is a schematic drawing showing a side view 250 of the short side 108 of a single component 100 of a multi-well plate insert.

Details of the protrusions/extensions 120 are provided in FIGS. 2A and 2B. Example conical protrusions/extensions 120 are shown and discussed, but other shapes can be used. As shown in FIG. 2A (side view 200 of a long side 112 of an example single component 100 of multi-well plate insert), and 2B (side view 250 of a short side 108 of a single component of a multi-well plate insert), the protrusions/extensions 120 have a depth 125 measured from the top surface 105 to the bottom of tip 130 of each protrusion/extension 120. The tip 130 is an angled or tapered terminal region at the distal end of the protrusion/extension 120 spaced away from the top surface by the length or depth 125 of the hollow shaft of the protrusion/extension 120. The depth 125 is such that the protrusions/extensions 120 rest inside each well of a well plate, but do not extend fully to the bottom of the wells of the well plate. In one example, the depth of the protrusions/extensions 120 is at least about 25 mm, such about 33.718 mm as shown in FIG. 1.

A side view 250 of individual component 100 is shown in FIG. 2A. The top surface 105 can include two side aprons 205 that extend vertically in the direction of tip 130 of the protrusions/extensions 120 beyond the perimeter wall 210 of the substantially planar top surface 105. A perimeter wall 210 can fit flush with a perimeter wall of one or more additional multi-well plate insert component parts 100. The side aprons 205 can be configured to rest outside the top surface 105 to help align the multi-well plate insert component part(s) 100. In some examples, the multi-well plate insert component parts 100 contains no side aprons 205.

As shown in FIGS. 2A and 2B, the protrusions/extensions 120, which can be substantially conical, contain holes or perforations 215, 216 that allow liquid in the multi-well plate to enter the interior of protrusions/extensions 120, which can be removed by pipetting. In one example, such holes are longitudinal holes or openings 215 (tough other shapes are possible, such as circular, oval, square or rectangular) extending vertically along the long axis of each protrusion/extension 120. In some example, there are 1, 2, 3, 4, 5, 6, or more longitudinal holes per protrusion/extension 120. The protrusions/extensions 120 include a tip 130 at the end opposite of top surface 105, which can include one or more terminal hole/perforations 216 (although one hole/perforation 216 is shown, more can be present, such as at least 1, at least 2 or at least three terminal holes/perforations 216). In some examples, the holes or perforations 215, 216 have a minimal open dimension 220 of at least about 0.6 mm, at least about 0.7 mm, at least about 0.8 mm, at least about 0.9 mm, or at least about 1 mm, such about 0.6 mm, about 0.7 mm, about 0.8 mm, about 0.9 mm, or about 1 mm.

From the long side view 200 of individual component 100 shown in FIG. 2A, an example substantially conical shape of hole/perforation 215 can be seen, with a wider opening at the top which angles toward tip 130. The tip 130 can also be a conical or rounded conical tip at the lower portion of a largely frustoconical protrusion. In the example shown in FIGS. 2A and 2B, the long side 112 of the individual component 100 shown in these examples contains eight columns and four rows of protrusions 120. As shown in FIG. 2B, the opening of two longitudinal holes 215 are visible on each protrusion/extension 120. One or more terminal holes/perforations 216 can also be present on each protrusion/extension 120. In some examples, round holes are contained solely within the angled tip 130 region, the region which narrows more steeply than the body of the protrusion 120, and do not extend lengthwise up the protrusion.

The protrusions/extensions 120 can also include ridges 222, which in the examples shown in FIGS. 2A and 2B are at tip 130 of the protrusions/extensions 120. Holes can further be located around, between, or among ridges 222. The ridges 222 can extend axially away from the central axis of the substantially conical tip 130. In some examples, the tip can be blunted (e.g., rounded, square, or flat)). Ridges can be configured to pierce a foil seal on a well plate.

As shown in FIG. 2B, from a view of a short side 250, ports or holes 225 are visible within the side apron 205. Ports 225 can be circular or oval holes useful for holding or handling a component 100 of the well plate insert, for example by a handling robot.

Figure 3A:
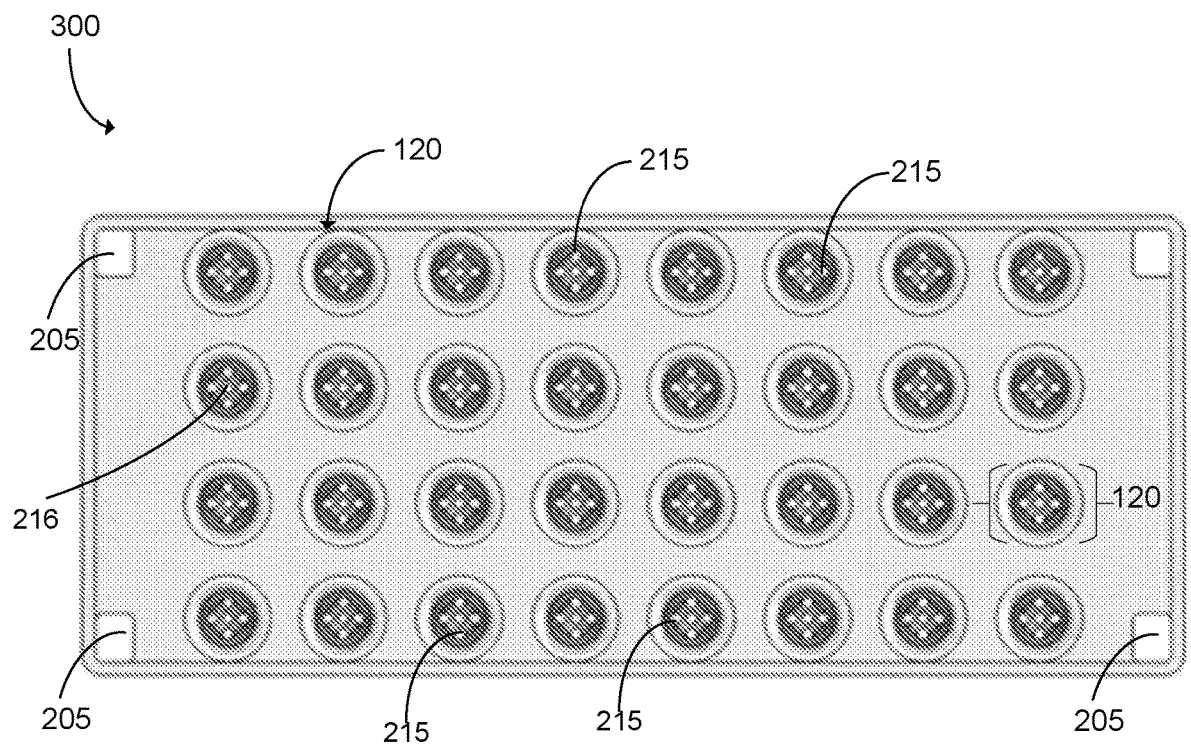
FIG. 3A is a schematic drawing showing, in one example, a top view 300 of a single component 100 of a multi-well plate insert.
Figure 3B:
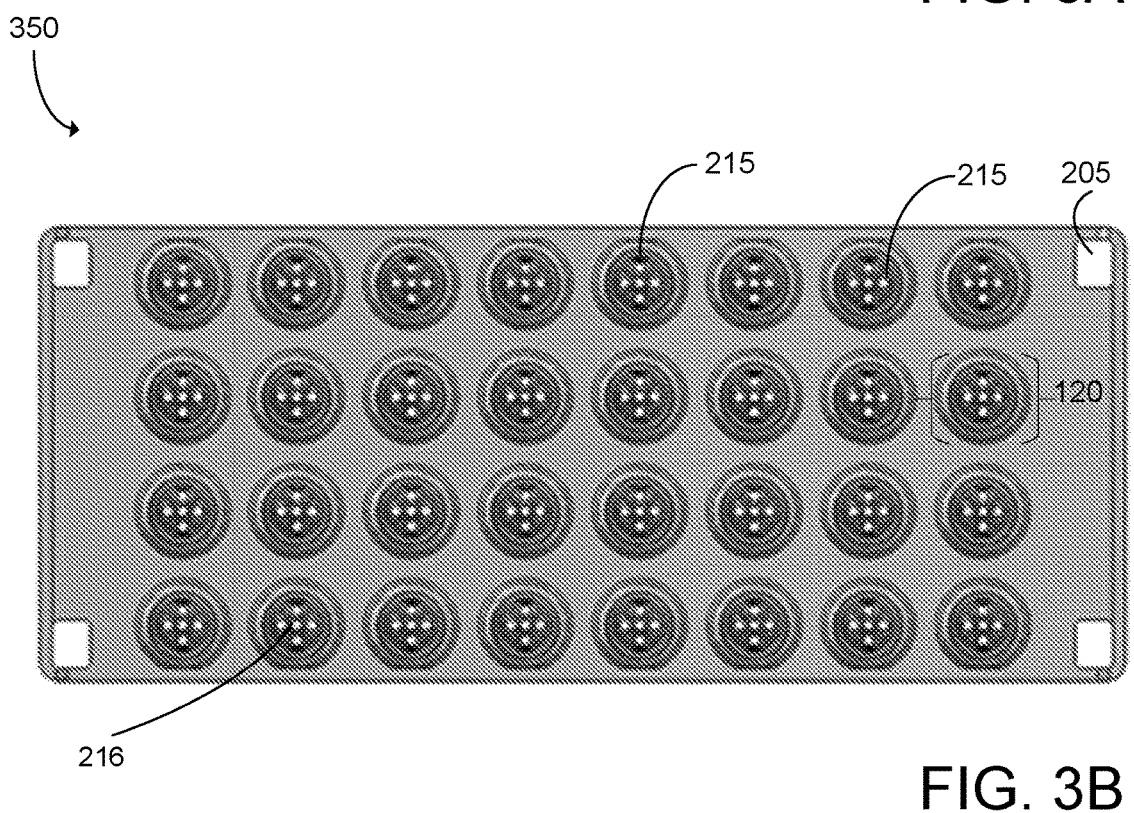
FIG. 3B is a schematic drawing showing, in one example, a bottom view 350 of a single component 100 of a multi-well plate insert.

FIG. 3A and FIG. 3B show a top 300 and bottom 350 view of a single component 100 of a multi-well plate insert, respectively. From top view 300 each of 32 protrusions/extensions 120 can be seen. Each protrusion/extension 120 is hollow to accommodate a pipette tip or other aspiration device. At the bottom of each protrusion/extension 120, holes/perforations 215, 216 can be present. A central hole/perforation 216 with four surrounding holes/perforations 215 is exemplified, but other arrangements are possible (such as a central hole/perforation 216 with 1, 2, 3, 4, 5, 6, 7, 8, 9, or 10 surrounding holes). The holes/perforations 215, 216 may be symmetrically around a central axis. In some examples, a central hole 216 is present. In some examples, five total holes/perforations 215, 216 are present at the tip 130 of each protrusion/extension 120. Each of the holes/perforations 215, 216 can also be seen from the bottom view 350 shown in FIG. 3B. In some examples, the central hole/perforation 216 is absent, and instead includes a closed point (e.g., sharp point), for example to enable piercing of a foil or other covering.

Figure 4:
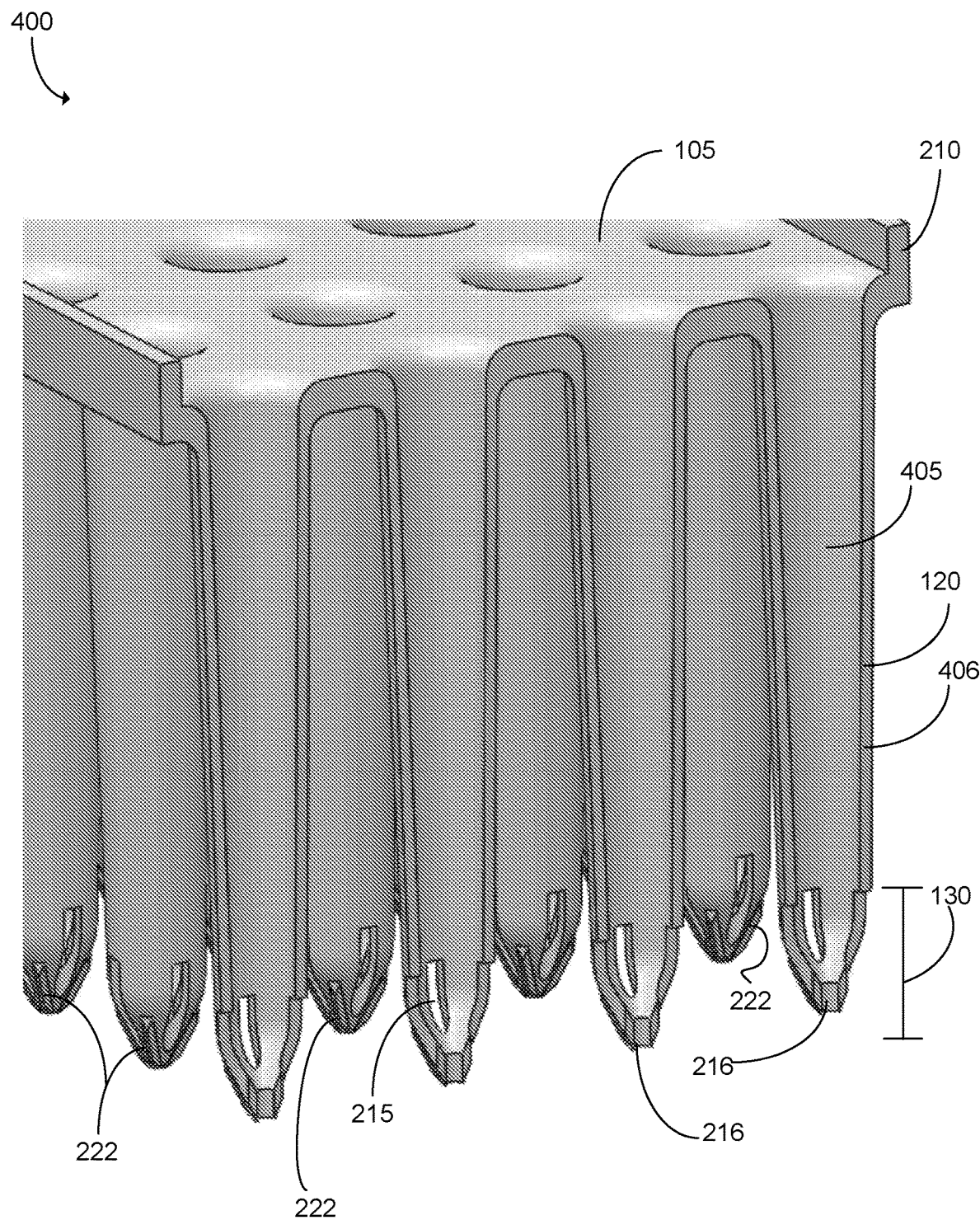
FIG. 4 is a schematic drawing showing, in one example, a cross-section 400 of the protrusions/extensions 120 of a single component 100 of a multi-well plate insert.

FIG. 4 shows a cross-section 400 and close up of example protrusions/extensions 120. The perimeter wall 210 of the component part 100 can be seen to surround the at least substantially planar top surface 105 can be contiguous with an exterior of the outer protrusions/extensions 120. In some examples, no raise perimeter wall 210 is present and the perimeter of the well plate insert component is of the same plane as the rest of the top surface 105. The at least substantially planar top surface 105 is broken by the hollow entry of each protrusion/extension 120. Each protrusion/extension 120 includes an exterior 406 and interior 405 component. The interior hollow cavity 405 of each protrusion/extension 120 is sized to accommodate a pipette tip (or other aspiration device) within the protrusion/extension 120. In the example shown in FIG. 4, in cross-section, the protrusions/extensions 120 include longitudinal holes/perforations 215 that radiate away from an optional central hole/perforation 216 at tip 130 of each protrusion/extension 120. In this example, the longitudinal holes/perforations 215 are at the tip 130 instead of in the body of the protrusion/extension 120 (e.g., contrast to FIGS. 1-3). The exterior of tip 130 includes one or more ridges 222. In the example shown, each protrusion/extension 120 includes four ridges 222. But other arrangements are possible, such as 1, 2, 3, 4, 5, 6, 7, 8, 9, or 10 individual ridges 222. The ridges can extend up along the length of a protrusion/extension 120, radiating outwardly form a central hole. In some example, tip 130 includes alternating ridges 222 and holes/perforations 215.

Figure 5:
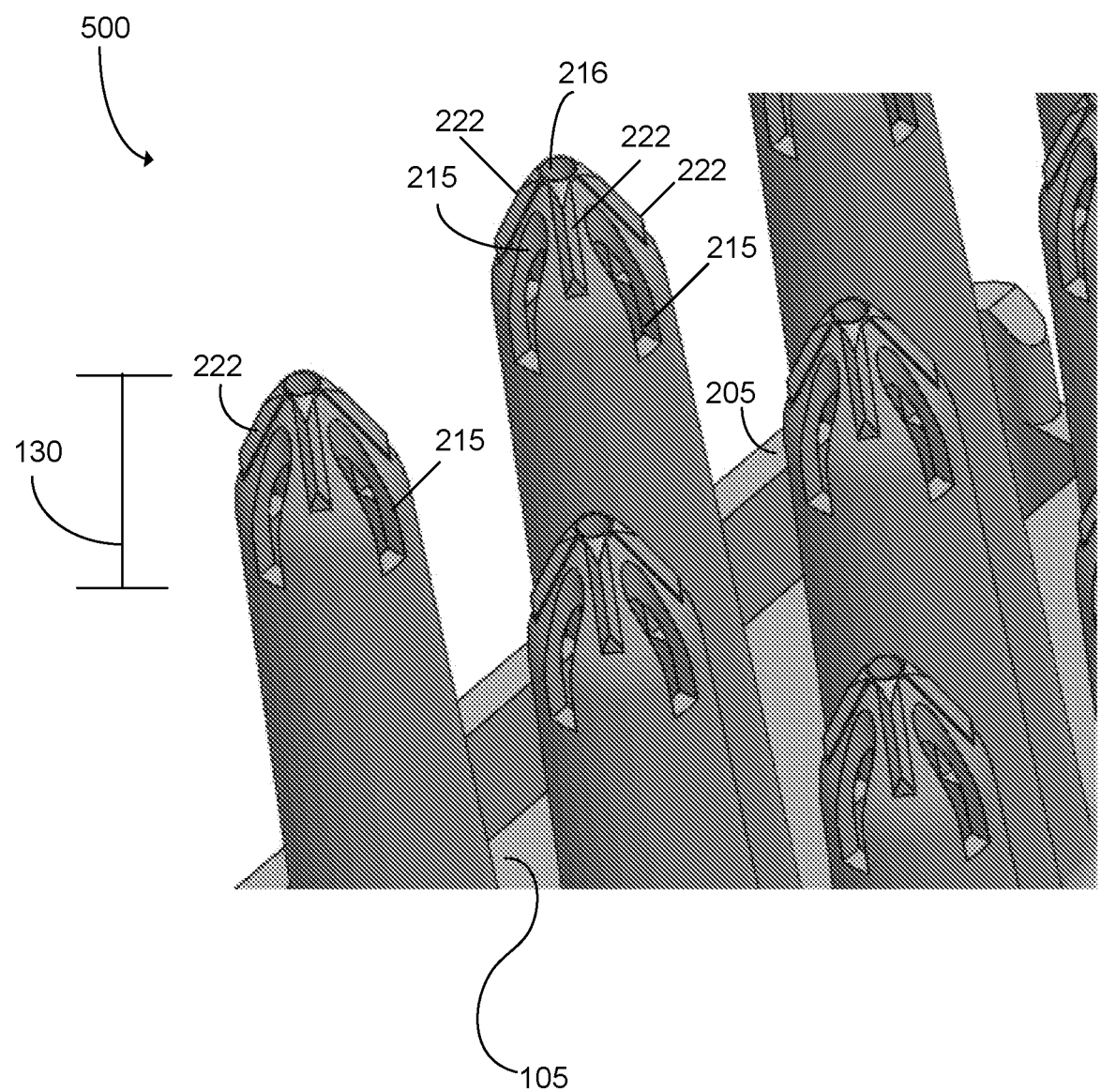
FIG. 5 is a schematic drawing showing, in one example, a close up view 500 of tip 130 of protrusions/extensions 120 of a multi-well plate insert.

FIG. 5 shows a close up view 500 of tip 130 of the protrusions/extensions 120 where the ridges 222 can be seen in greater detail. In the examples shown in FIG. 5, holes/perforations 215 are shown to radiate away from an optional central hole/perforation 216 extending along protrusion/extension 120 toward the planar top surface 105 of the insert. In some examples, optional central hole/perforation 216 is circular. In some examples, holes/perforations 215 are longitudinal. In some examples, the optional central hole/perforation 216 and holes/perforations 215 have a diameter of at least 0.6 mm, such as at least 0.7 mm, at least 0.8 mm, at least 0.9 mm, or at least 1 mm, such as about 0.6 mm, such as about 0.7 mm, about 0.8 mm, about 0.9 mm, or about 1 mm. Holes/perforations 215 can be confined to the tip region 130 or extend any length along the protrusion/extension 120. The ridges 222 also extend radially away from an optional one or more central holes or openings 216 (which can be circular). The ridges are shown interspersed among longitudinal holes 215. The ridges 222 can be blade shaped, extending away from a surface of tip 130 as an angled spine. In some examples ridges 222 fit between the longitudinal holes 215. In cross section, the ridges 22 can be triangular, with a 90 degree angle.

Ridges 222 can assist in the puncture, or tearing of a previously punctured sealed foil top of a well plate. Ease of insertion of the well plate insert with minimal resistant of the sealed foil top minimizes splashing of liquid contents of the wells of the well plates. Splashing can result in diminished solution volume, well cross-contamination, or contamination of assay components.

Figure 6A:
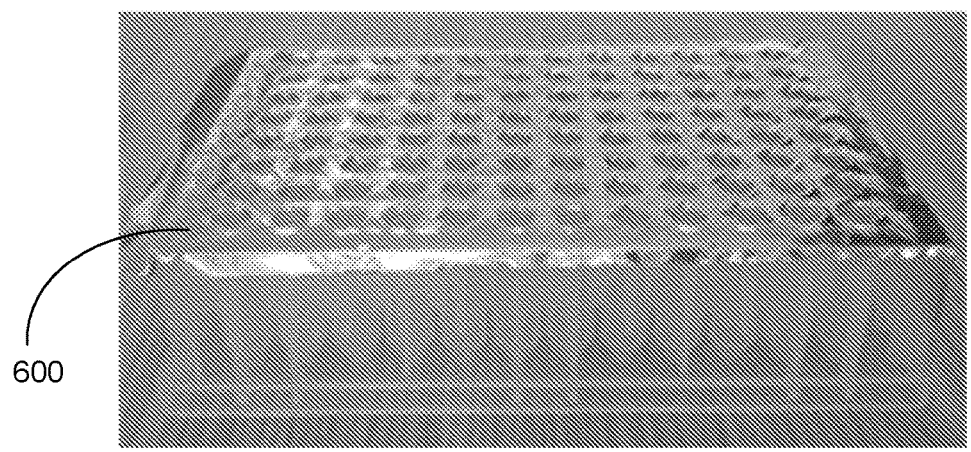
FIG. 6A shows, in one example, a foil covered multi-well plate 600.
Figure 6B:
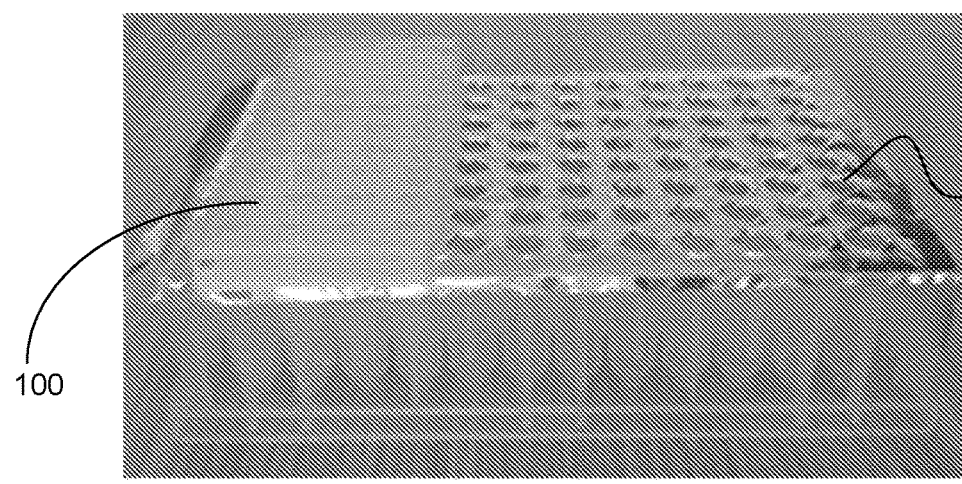
FIG. 6B shows, in one example, a single component 100 of a multi-well plate insert nested within the multi-well plate 600.
Figure 6C:
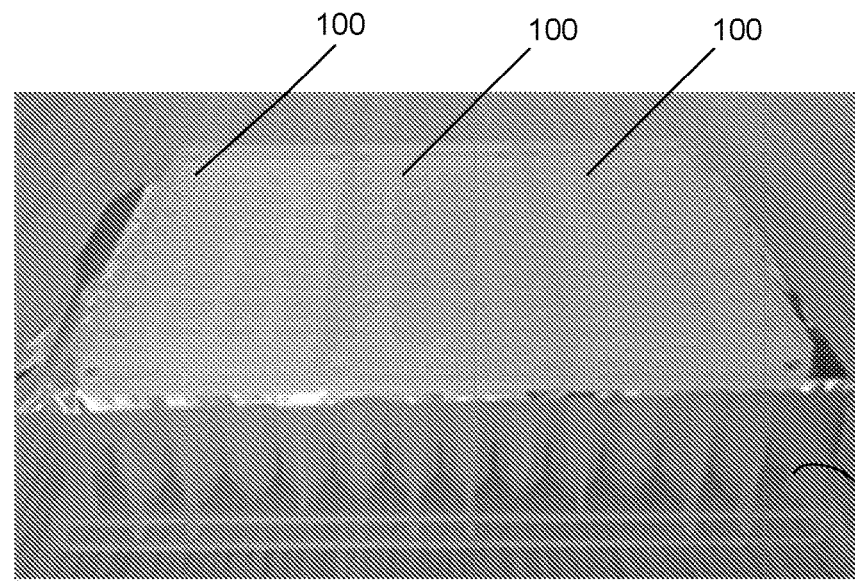
FIG. 6C shows, in one example, three components 100 of a multi-well plate insert nested within a multi-well plate.
Figure 7:
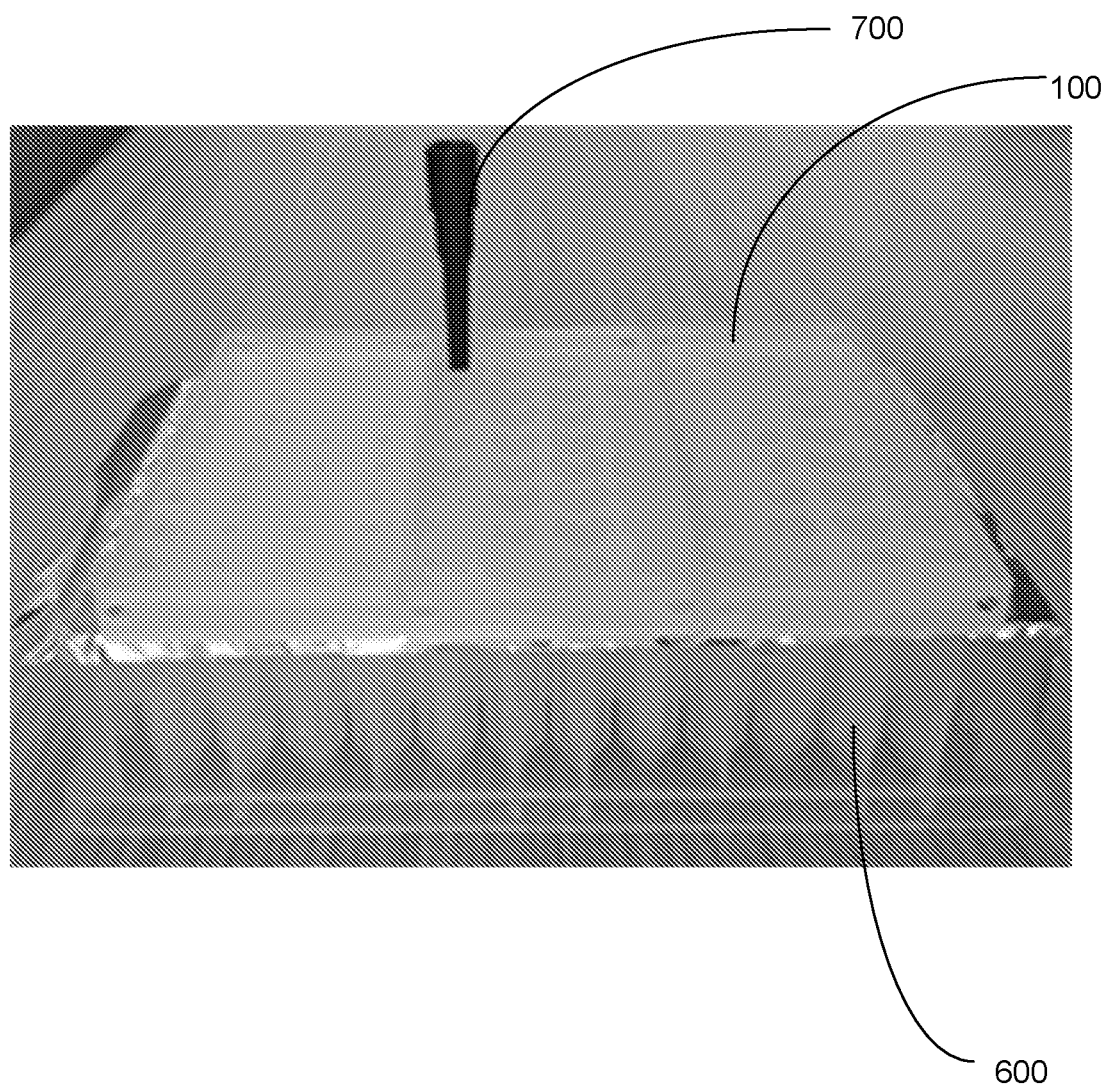
FIG. 7 shows, in one example, a pipette tip 700 fitted inside a protrusion/extension 120 of a multi-well plate insert 100 nested within a multi-well plate 600.

FIGS. 6A-6C show how one or more single components 100 are used with a multi-well plate in one example. The use of three individual single components 100 with a 96-well plate is shown. FIG. 6A shows a multi-well plate with a foil covering or seal 600 that has been perforated (for example with a pipette tip). FIG. 6B shows a single component 100 of a multi-well plate insert nested within one third of the wells (e.g., 32 wells) of a 96-well plate. FIG. 6C shows three individual single components 100 fitted side-by-side to occupy each well of the 96-well plate 600. FIG. 7 shows that a pipette tip 700 may be inserted into a protrusion/extension 120 of the single component 100 of the multi-well plate insert 100.

The single components of the multi-well plate insert can be manufactured using a three-dimensional (3D) printer, an injection mold, or both. In some examples, the multi-well plate insert is manufactured using a 3D printer or an injection mold without the port/hole 225, holes/perforations 215, and/or or optional central hole/perforation 216, but instead such openings are added subsequently.

The single components of the multi-well plate insert can be composed of polypropylene, polyethelene, polycarbonate, or mixtures thereof. In one example, the single components of the of a multi-well plate insert are composed of an organic polymer. Example materials include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof). In one example, the single components of the of a multi-well plate insert are composed of materials that have low nucleic acid binding properties.

Also provided are kits that include one or more multi-well inserts (or component part thereof). In some examples, such kits also include a multi-well plate. Thus, in some examples, the kit includes a multi-well plate adaptor designed for use with a 96-well plate (such as three adaptors), and a 96-well plate. Other kits can include particular numbers of multi-well plate adaptors and their corresponding multi-well plate, such as 1 adaptor with a 6-well plate, 1 adaptor with a 12-well plate, 1 or 2 adaptors with a 24-well plate, 1, 2 or 3 adaptors with a 48-well plate, or 12 adaptors with a 384-well plate. In some examples, such kits also include pipette tips. In some examples, such kits also include a buffer to extract nucleic acid molecules, for example from a DBS or FFPE sample. In some examples, such kits also include a lysis buffer, such as one that includes a detergent.

Methods of Use

Also provided herein are methods of using the disclosed multi-well plate inserts, for example in methods that include obtaining or collecting a liquid, such as a lysate containing one or more target biological molecules (such as a nucleic acid molecule or protein). For example, the method can include adding or placing one or more of the disclosed multi-well plate inserts on top of a multi-well plate containing a lysate (such as one generated from a DBS or FFPE sample), such that the extensions/protrusions of the multi-well plate inserts are introduced into the wells of the multi-well plate. In some examples, this is done manually, and in other examples this is done robotically. In some examples, one or more disclosed multi-well plate inserts lock onto the multi-well plate. However, in some examples the one or more disclosed multi-well plate inserts simply sit on top of the multi-well plate. This allows the liquid (e.g., lysate), but not debris, in the well of the multi-well plate to flow into the extensions or protrusions via the holes/perforations. The method can then include introducing a pipette tip into each extension/protrusion, which now contains the liquid that was present in the well, to allow for collection of the liquid (e.g., lysate), without collecting the debris. Thus, the method can include removal or collection of the liquid (e.g., lysate), without collecting the debris. In some examples, the volume of liquid collected after introduction of one or more disclosed multi-well plate inserts into the multi-well plate is at least 50 uL, at least 100 uL, at least 150 uL, at least 200 uL, at least 300 uL, at least 500 uL, at least 600 uL, such as about 150 uL, about 300 uL or about 600 uL.

The disclosed multi-well plate inserts are inserted into the multi-well plate such that each well of the multi-well plate includes one extension/protrusion therein.

In some examples, prior to adding or placing one or more of the disclosed multi-well plate inserts on top of a multi-well plate containing a liquid (e.g., lysate), for example if the multi-well plate includes a piercable covering (such as a foil), the method can include piercing the covering, for example with pipette tips, which introduces a hole in the covering, allowing access to the contents of the wells. The introduced hole can then be used as a point of entry for the extensions/protrusions of the multi-well plate inserts. The ridges on the extensions/protrusions may assist in this.

In some examples, prior to adding or placing one or more of the disclosed multi-well plate inserts on top of a multi-well plate containing a liquid (e.g., lysate), samples (e.g., DBS, tissue samples, FFPE samples) in the wells are processed. For example, cells can be lysed (e.g., with heat, such as at least about 40° C., at least about 50° C., at least about 60° C., at least about 70° C., at least about 65° C., at least about 70° C., at least about 80° C., or at least about 90° C., and/or detergent), undesirable molecules degraded (e.g., with a protease or nuclease), target molecules manipulated (e.g., nucleic acid molecules may be amplified, for example with PCR), or combinations thereof. In some examples, prior to adding or placing one or more of the disclosed multi-well plate inserts on top of a multi-well plate containing a liquid (e.g., lysate), for example if the multi-well plate includes a piercable covering (such as a foil), the method can include piercing the covering, for example with pipette tips, which introduces a hole in the covering, allowing access to the contents of the wells. The introduced hole can then be used as a point of entry for the extensions/protrusions of the multi-well plate inserts. The ridges on the extensions/protrusions may assist in this.

In some examples, the multi-well plate includes a solid support in each well, such as a bulk material, such as a paper (such as a filter paper), membrane, porous material, water immiscible gel, water immiscible ionic liquid, water immiscible polymer (such as an organic polymer), and the like. For example, the well can contain a membrane, such as nitrocellulose. In a specific example the solid support is an FTA® card.

In some examples, the multi-well plate includes DBS in the wells. For example, FTA™ cards containing blood samples can be introduced into 96-well plate using the Hamilton EasyPunch STARlet system. In one example, the well includes a filter paper disk (such as from Whatman™ FTA™ cards) containing a dried blood sample from a subject. In some examples, the support containing the blood sample is about 3 mm in diameter.

In some examples, the multi-well plate includes a lysate containing a DNA library.

In some examples, the multi-well plate includes an FFPE sample in the wells. For example, FFPE tissue samples, such as an FFPE slice or curl containing tissue can be in a multi-well plate. In some examples, the multi-well plate includes a fresh tissue, or tissue obtained from a slide (e.g., tissue scrape). The tissue can be any tissue of interest, such as tissue from the skin, colon, lung, liver, kidney, pancreas, CNS, brain, muscle, breast, prostate, uterus, cervix, ovary, and the like. In one example, the tissue is a tumor sample (such as a liquid or solid tumor sample). Example tumors, such as cancers, that can be as source of material for analysis with the disclosed inserts include solid tumors, such as breast carcinomas (e.g. lobular and duct carcinomas), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, and lymphatic tumors (including B-cell and T-cell malignant lymphoma). In one example, the tumor is an adenocarcinoma. Example tumors, such as cancers, that can be as source of material for analysis with the disclosed inserts include liquid tumors, such as a lymphatic, white blood cell, or other type of leukemia. In a specific example, the tumor treated is a tumor of the blood, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), lymphomas (such as Hodgkin's lymphoma and non-Hodgkin's lymphoma), and myelomas).

In some examples, the multi-well plate includes a solid support (such as paper or nitrocellulose) containing a sample from a non-human source, such as an environmental sample (e.g., water, air, or soil sample) in the wells. For example, such sources can be analyzed for the presence of a target pathogen, such as a virus, bacterium, parasite, or fungus. In some examples, the support containing the sample is about 3 mm in diameter.

The well can also include a liquid, such as a buffer that allows for lysis of cells, extraction or isolation of a target molecule (such as a target protein or nucleic acid molecule, such as DNA, RNA or antibodies), and the like. In one example, the liquid in the well contains nucleic acid molecules that can be sequenced (such as a sequencing library), for example using next generation sequences (NGS). In some example, the liquid includes proteinase K or other enzyme to degrade undesired proteins.

In some example, the method is muliplexed. For example, each well of the multi-well plate can contain samples from different patients (or sources), different samples from the same patients (or source), or combinations thereof.

Example 1

Extraction of DNA

This example describes methods use to extract DNA from blood samples using a well plate insert as described herein.

Figure 8A:
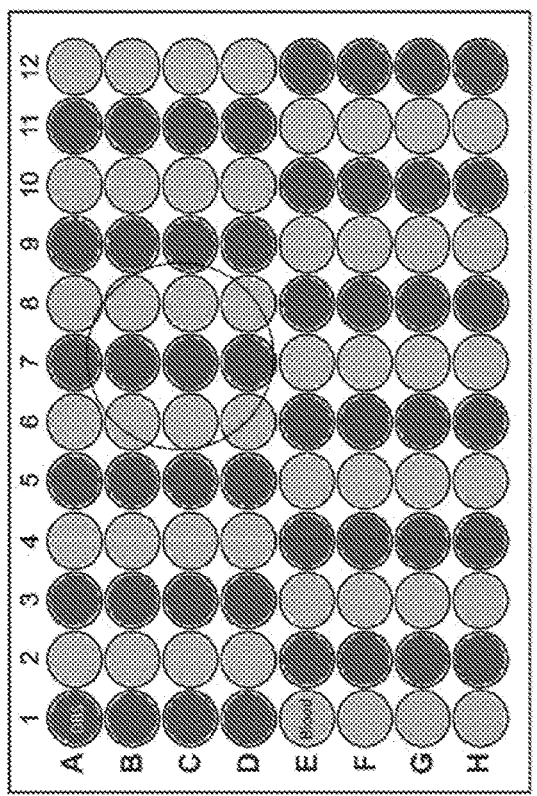
FIG. 8A is a schematic showing, in one example, an overview of how blood samples were analyzed.
Figure 8A:
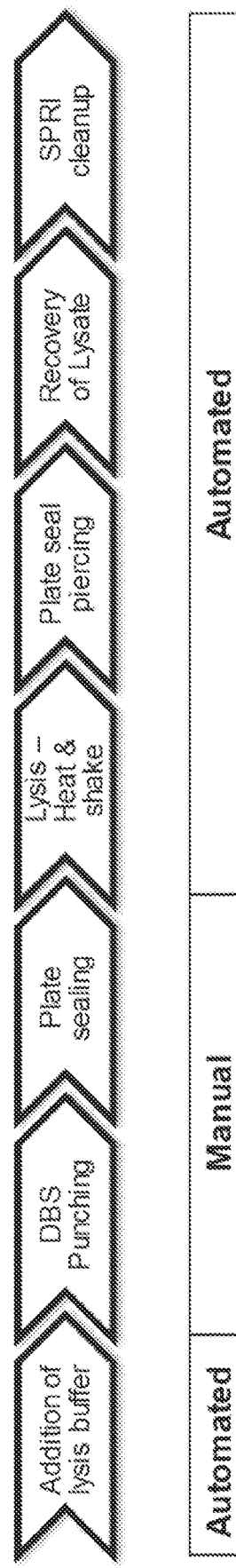

Samples (12 DBS, 12 liquid blood) were analyzed as shown in FIG. 8A. For each DBS sample, there were five punches per well in a multi-well plate. Liquid blood included 12 uL of blood per well in a multi-well plate. 12 DBS and 12 blood samples were arranged in quadruplicate intermingled around the well plate. Standard DNA extraction protocols were used with lysing, lysate recovery, and Solid Phase Reversible Immobilization (SPRI) cleanup steps being automated. Briefly, lysis buffer was added to each well. Following lysis, the insert was introduced into the multi-well plate, and the lysate removed and analyzed for DNA yield. The amount of DNA obtained from each well was determined.

Figure 8B:
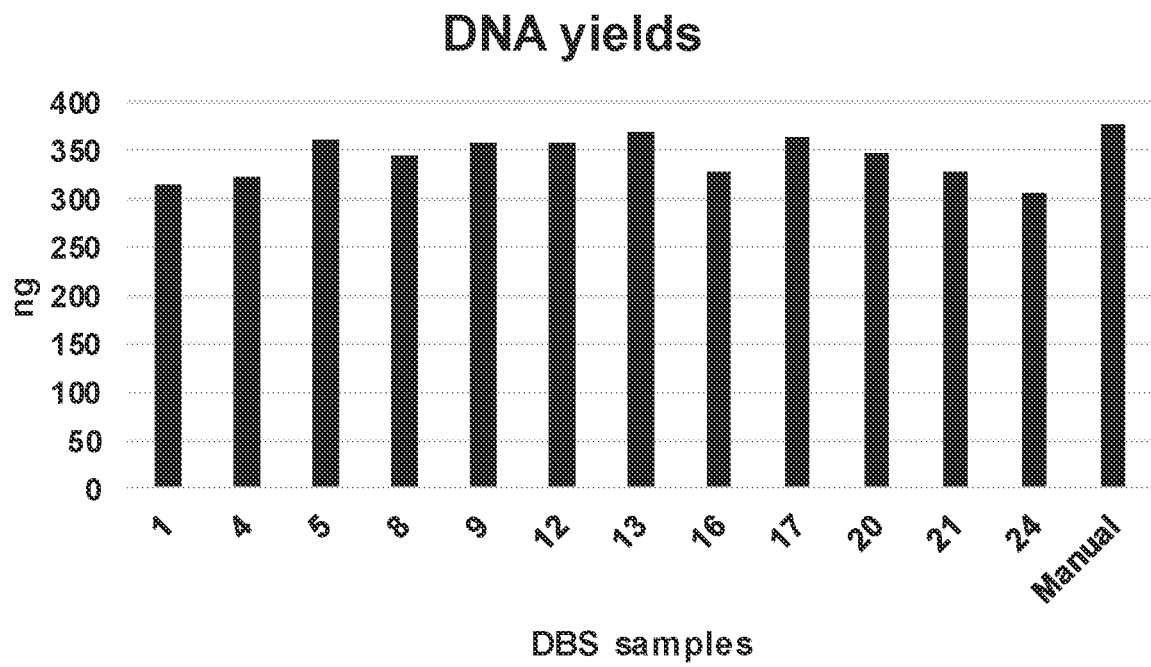
FIG. 8B is a bar graph showing, in one example, DNA recovery using DBS samples and the disclosed multi-well plate insert.
Figure 8C:
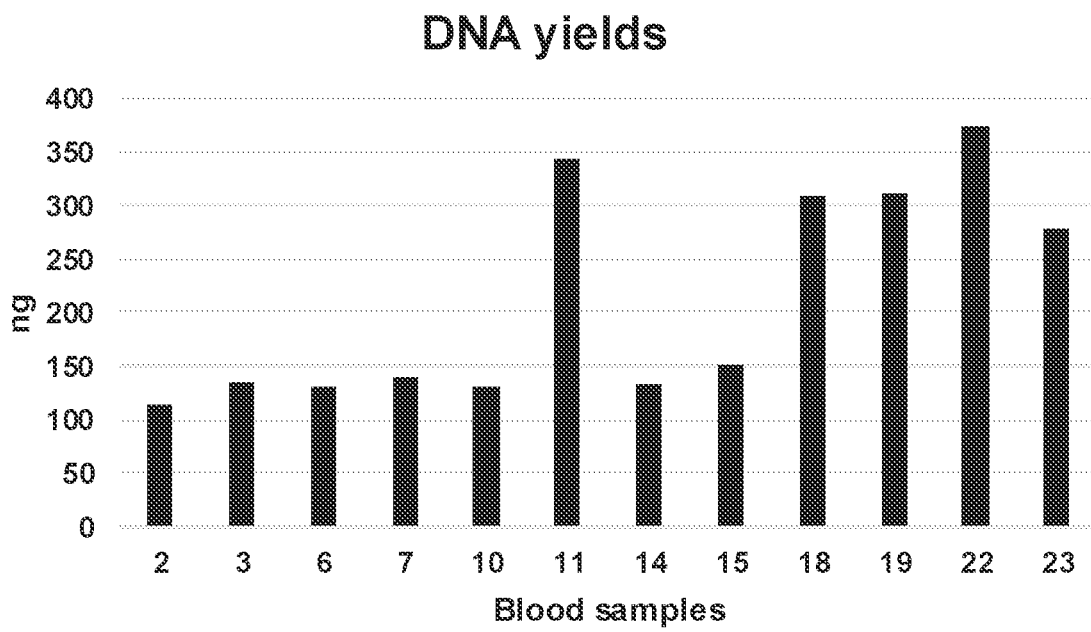
FIG. 8C is a bar graph showing, in one example, DNA recovery using liquid blood samples and the disclosed multi-well plate insert.

The multi-well plate insert successfully separated the solid debris of a DBS, and debris resulting from preparation of the liquid blood sample, from the pipette tip of a liquid handling robot used for solution aspiration. As shown in Table 1 (and FIGS. 8B-8C), DNA extraction assays using robotic sample handling contained similar DNA quantities from both liquid blood and DBS within a well plate. This assay took about 2 hr and 40 minutes to complete.

TABLE 1

DNA Yields

| Sample No. | Donor ID | Type | Qubit HS ng/ul | ng |
|---|---|---|---|---|
| 1 | CS658 | DBS | 6.269 | 313.45 |
| 2 | CS658 | Blood | 2.3 | 115 |
| 3 | CS658 | Blood | 2.7 | 135 |
| 4 | CS658 | DBS | 6.44 | 322 |
| 5 | CS658 | DBS | 7.2 | 360 |
| 6 | CS658 | Blood | 2.62 | 131 |
| 7 | CS658 | Blood | 2.8 | 140 |
| 8 | CS658 | DBS | 6.88 | 344 |
| 9 | CS658 | DBS | 7.16 | 358 |
| 10 | CS658 | Blood | 2.58 | 129 |
| 11 | CS658 | Blood | 6.86 | 343 |
| 12 | CS658 | DBS | 7.16 | 358 |
| 13 | CS658 | DBS | 7.36 | 368 |
| 14 | CS658 | Blood | 2.64 | 132 |
| 15 | CS658 | Blood | 3.04 | 152 |
| 16 | CS658 | DBS | 6.54 | 327 |
| 17 | CS658 | DBS | 7.28 | 364 |
| 18 | CS658 | Blood | 6.16 | 308 |
| 19 | CS658 | Blood | 6.2 | 310 |
| 20 | CS658 | DBS | 6.94 | 347 |
| 21 | CS658 | DBS | 6.56 | 328 |
| 22 | CS658 | Blood | 7.46 | 373 |
| 23 | CS658 | Blood | 5.56 | 278 |
| 24 | CS658 | DBS | 6.1 | 305 |

Figure 9A:
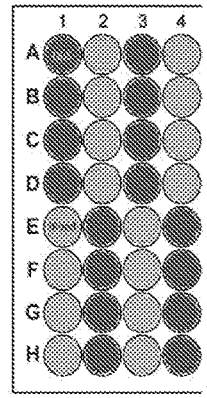
FIG. 9A is a schematic showing, in one example, an overview of how blood samples were analyzed.
Figure 9A:
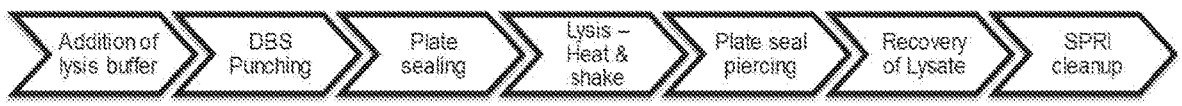
Figure 9A:
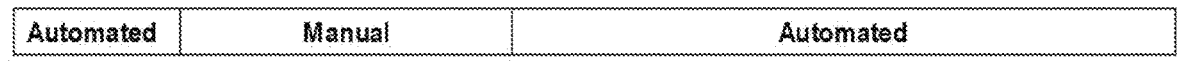

In a second experiment, samples (4 DBS, 4 liquid blood) were analyzed as shown in FIG. 9A. For each DBS sample, there were five punches per well in a multi-well plate. Liquid blood included 12 uL of blood per well in a multi-well plate. 4 DBS and 4 blood samples were arranged in quadruplicate intermingled around the well plate (FIG. 9A). Standard DNA extraction protocols were used with lysing, lysate recovery, and Solid Phase Reversible Immobilization (SPRI) cleanup steps being automated. Briefly, the foil on the multi-well plate was pierced with pipette tips, and 200 μL of lysis buffer was added to each well. Following lysis, the insert was introduced into the multi-well plate, and the lysate removed and analyzed for DNA yield. The amount of DNA obtained from each well was determined using Qubit quantitation.

Figure 9B:
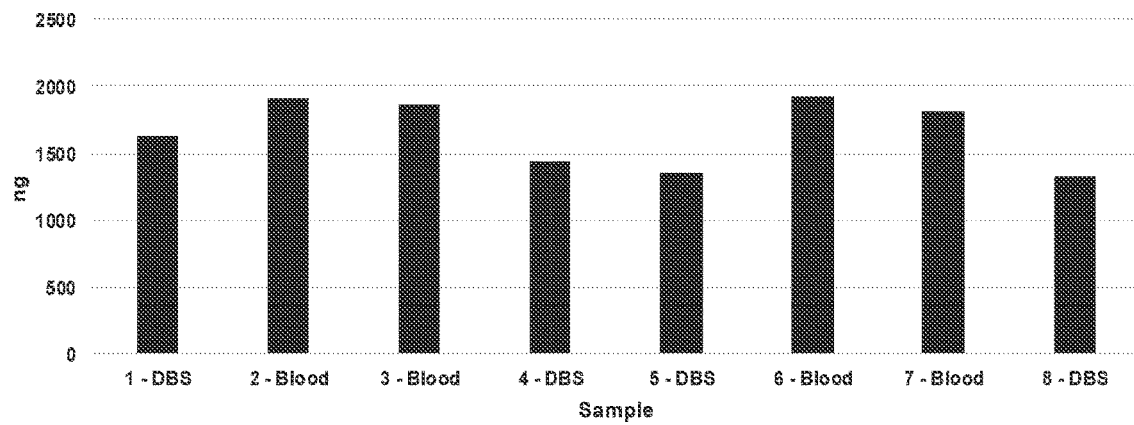
FIG. 9B is a bar graph showing, in one example, DNA recovery using DBS and liquid samples and the disclosed multi-well plate insert.

The multi-well plate insert successfully separated the solid debris of a DBS, and debris resulting from preparation of the liquid blood sample, from the pipette tip of a liquid handling robot used for solution aspiration. As shown in FIG. 9B, DNA extraction assays using robotic sample handling contained similar DNA quantities from both liquid blood and DBS within a well plate.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

In view of the many possible examples to which the principles of the disclosure may be applied, it should be recognized that the illustrated examples are only examples of the disclosure and should not be taken as limiting the scope of the invention. Rather, the scope of the invention is defined by the following claims. We therefore claim as our invention all that comes within the scope and spirit of these claims.

We claim:

1. A multi-well plate adaptor for use with a multi-well plate having wells, the multi-well plate adapter comprising:

two or more component parts, each component part comprising:
   a top surface; and
   hollow conical protrusions extending from the top surface, the conical protrusions having a shape that matches a corresponding well of the multi-well plate to allow the conical protrusions to be inserted within the corresponding well of the multi-well plate, an axis of each of the conical protrusions being substantially perpendicular to the top surface; and
   each hollow conical protrusion comprising an angled tip at an end of the corresponding conical protrusion that is distal from the top surface, the angled tip comprising one or more holes, an outer surface, and one or more ridges on the outer surface of the angled tip.

2. The multi-well plate adaptor of claim 1, wherein the multi-well plate is a 96-well plate.

3. The multi-well plate adaptor of claim 2, comprising three component parts.

4. The multi-well plate adaptor of claim 3, wherein the top surface has a length of between about 75 mm and about 95 mm and a width of between about 20 mm and about 30 mm.

5. The multi-well plate adaptor of claim 1, wherein a distance that each hollow conical protrusion extends from the top surface is shorter than a depth of the wells of the multi-well plate.

6. The multi-well plate adaptor of claim 5, wherein the distance each hollow conical protrusion extends from the top surface is between about 15 mm and about 30 mm.

7. The multi-well plate adaptor of claim 1, wherein the hollow conical protrusions have an inner diameter that can accommodate a pipette tip.

8. The multi-well plate adaptor of claim 1, wherein the one or more holes of the angled tip has a dimension of between about 0.6 mm and about 0.8 mm.

9. The multi-well plate adaptor of claim 1, wherein the one or more holes of the angled tip comprises a central hole at the end and multiple longitudinal holes radiating symmetrically from the central hole, each of the longitudinal holes separated by a portion of the angled tip, and wherein the portion of the angled tip separating each of the longitudinal holes further comprises the one or more ridges on the outer surface of the angled tip, wherein the central hole has a diameter of between about 0.6 mm and about 1 mm and the longitudinal holes comprise a dimension of between about 0.6 mm and about 1 mm.

10. A well plate insert for use with a well plate having wells, the well plate insert, comprising:
   two or more insert components, each insert component comprising:
      a rectangular top surface;
      hollow extensions protruding from the top surface, the hollow extensions having a shape that matches a corresponding well of the well plate to allow the hollow extensions to be inserted within the corresponding well of the well plate, wherein a main axis of each of the hollow extensions is at least substantially perpendicular to a plane of the rectangular top surface;
      the hollow extensions having a distal tip with one or more perforations;
      the distal tip further comprising an outer surface comprising one or more ridges extending away the distal tip; and
      the rectangular top surface of one of the insert components having a long edge that is adapted to fit with a long edge of the rectangular top surface of another one of the insert components.

11. The well plate insert of claim 10, wherein the hollow extensions have a main body and a smaller diameter end, the main body is an elongate frusto-conical extension and the distal tip extends substantially conically from the smaller diameter end of the hollow extension.

12. The well plate insert of claim 11, wherein the main body of the hollow extensions comprises a solid surface.

13. The well plate insert of claim 11, wherein the one or more ridges do not extend beyond the distal tip onto the main body of the hollow extensions.

14. The well plate insert of claim 10, wherein the hollow extensions do not comprise a mesh or fiber insert.

15. The well plate insert of claim 10, wherein each perforation has a dimension of between about 0.6 mm and about 0.8 mm.

16. The well plate insert of claim 10, wherein the one or more ridges of the distal tip are capable of piercing a seal of the well plate.

17. The well plate insert of claim 10, wherein the one or more perforations are sized to allow a lysate to flow through and to prevent passage of a particulate in a well of the well plate.

18. The well plate insert of claim 10, wherein the hollow extensions for each insert comprises 32 hollow extensions arranged in a grid with four hollow extensions along a short edge of the rectangular top surface and eight hollow extensions along the long edge of the rectangular top surface.

19. The well plate insert of claim 18, adapted to nest on top of a 96-well plate with the hollow extensions protruding into each individual well.

20. A lysate isolation plate adaptor for use with a multi-well plate having wells, the plate adapter comprising:
   three identical components parts, each comprising;
      a planar rectangular main body with 32 elongate extensions protruding in a grid pattern therefrom, the extensions having a shape that matches a corresponding well of the multi-well plate to allow the extensions to be inserted within the corresponding well of the multi-well plate,
   wherein a main axis of each elongate extension is at least substantially perpendicular to the planar rectangular main body;
      each elongate extension having a rounded tip comprising an exterior surface and a plurality of holes, each hole having a dimension of between about 0.6 mm and about 0.8 mm; and
      one or more angled spines on the exterior surface of the rounded tip.

21. An apparatus, comprising:
   a well plate having wells, each well having an opening;
   liquid contained in the wells;
   a seal covering the openings; and
   a well plate adaptor comprising:
      a top surface; and
      hollow conical protrusions extending from the top surface, the conical protrusions having a shape that matches a corresponding well of the well plate to allow the conical protrusions to be inserted within the corresponding well of the well plate, each hollow conical protrusion comprising an angled tip that is distal from the top surface, the angled tip comprising one or more holes, an outer surface, and one or more ridges on the outer surface.

22. The apparatus of claim 21, wherein the well plate adapter is to nest with the well plate.

23. The apparatus of claim 21, wherein the ridges are to pierce or pass through the seal.

24. The apparatus of claim 21, wherein each of the angled tips has a central axis and wherein the one or more ridges of each of the conical protrusions comprises four ridges that extend axially away from the central axis.

25. The apparatus of claim 24, wherein the one or more openings of each of the conical protrusions comprise four openings and wherein one of the openings is positioned between pairs of the ridges.

* * * * *

UNITED STATES PATENT AND TRADEMARK OFFICE
CERTIFICATE OF CORRECTION

| | |
|---|---|
| PATENT NO. | : 11,351,551 B2 |
| APPLICATION NO. | : 16/626138 |
| DATED | : June 7, 2022 |
| INVENTOR(S) | : Andrew Joad et al. |

It is certified that error appears in the above-identified patent and that said Letters Patent is hereby corrected as shown below:

In the Specification

In Column 1, Line 6, delete "U.S.C." and insert -- U.S.C.§ --, therefor.

In the Claims

In Column 19, Line 66, Claim 10, delete "extending away the distal" and insert -- extending away from the distal --, therefor.

Signed and Sealed this
Fifteenth Day of November, 2022

Katherine Kelly Vidal
*Director of the United States Patent and Trademark Office*